United States Patent [19]

Liboff

[11] Patent Number: 5,059,298
[45] Date of Patent: Oct. 22, 1991

[54] METHOD AND APPARATUS FOR REGULATING TRANSMEMBRANE ION MOVEMENT

[75] Inventor: Abraham R. Liboff, Birmingham, Mich.

[73] Assignee: Life Resonances, Inc., Bozeman, Mont.

[21] Appl. No.: 278,688

[22] Filed: Dec. 1, 1988

Related U.S. Application Data

[63] Continuation-in-part of Ser. No. 923,760, Oct. 27, 1986.
[51] Int. Cl.$^5$ ............................................. B65D 85/18
[52] U.S. Cl. ............................................. 204/299 R
[58] Field of Search ................. 204/193, 155, 157.15, 204/164, 180.1; 435/173

[56] References Cited

U.S. PATENT DOCUMENTS

| | | | |
|---|---|---|---|
| 3,566,877 | 3/1971 | Smith | 128/422 |
| 3,890,953 | 6/1975 | Kraus et al. | |
| 3,893,462 | 7/1975 | Manning | |
| 3,911,930 | 10/1975 | Hagfors et al. | |
| 3,952,751 | 4/1976 | Yarger | |
| 4,105,017 | 8/1978 | Ryaby et al. | |
| 4,266,532 | 5/1981 | Ryaby et al. | |
| 4,428,366 | 1/1984 | Findl et al. | |
| 4,459,988 | 7/1984 | Dugot | |
| 4,535,775 | 8/1985 | Brighton et al. | |
| 4,548,208 | 10/1985 | Niemi | 128/419 F |
| 4,561,426 | 12/1985 | Stewart | 128/1.5 |
| 4,600,010 | 7/1986 | Dugot | |
| 4,616,629 | 10/1986 | Moore | |
| 4,622,952 | 11/1986 | Gordon | |
| 4,622,953 | 11/1986 | Gordon | |
| 4,654,574 | 3/1987 | Thaler | 320/14 |
| 4,683,873 | 8/1987 | Cadossi et al. | 128/1.5 |
| 4,757,804 | 7/1988 | Griffith et al. | 128/1.5 |
| 4,818,697 | 4/1989 | Liboff | 204/157.15 |
| 4,911,686 | 3/1990 | Thaler | 128/419 F |

OTHER PUBLICATIONS

Liboff, A. R., "Cyclotron Resonance in Membrane Transport," Interactions Between Electromagnetic Fields and Cells, Plenum Publishing Corp. (1985).

Liboff, A. R., "Geomagnetic Cyclotron Resonance in Living Cells," Journal of Biological Physics, vol. 13 (1985).

Blackman et al., "Effect of ELF (1–20Hz) and Modulated (50 Hz) RF Fields on the Efflux of Calcium Ions from Brain Tissue in Vitro," *Bioelectromagnetica* 6: 1–11 (1985).

"A Role for the Magnetic Field in the Radiation-Induced Efflux of Calcium Ions from Brain Tissue in Vitro," *Bioelectromagnetics*, 6: 327–337 (1985).

"Bioelectrochemical Studies of Implantable Bone Stimulation Electrodes", Bioelectrochemistry and Bioenergetics 5, 232–238 (1978).

"Clinical Experiences with Low Intensity Direct Current Stimulation of Bone Growth", Becker, Spadaro and Marino; Clinical Orthopedics and Related Research; No. 124; May 1977.

"Inducing Bone Growth in Vivo by Pulse Stimulation", Levy and Rubin; Clinical Orthopedics and Related Research; No. 88; Oct., 1972.

"Interactions Between Electromagnetic Fields and Cells", Chiabrera, Nicolini and Schwan; Plenum Publishing Corporation, 1985.

"Stimulation of Fracture Healing with Electromagnetic Fields of Extremely Low Frequency (EMF or ELF)", Wahlstrom; Clinical Orthopedics and Related Research; No. 186; Jun., 1984.

*Primary Examiner*—John F. Niebling
*Attorney, Agent, or Firm*—Dykema Gossett

[57] ABSTRACT

An improved apparatus and method for regulating transmembrane ion movement through a biochemical membrane. The apparatus includes a magnetic field generator and a magnetic field detector for producing a controlled, fluctuating, directionally oriented magnetic field parallel to a predetermined axis projecting through the membrane. The field detector samples the magnetic flux density along the predetermined access and provides a signal to a microprocessor which determines the average value of the flux density. This ratio is maintained by adjusting the frequency of the fluctuating magnetic field and/or by adjusting the intensity of the applied magnetic field as the composite magnetic flux density changes in response to changes in the local magnetic field to which the target membrane is subjected. By maintaining these precise predetermined ratios of frequency to average magnetic flux density, ion transport is controlled.

6 Claims, 2 Drawing Sheets

METHOD AND APPARATUS FOR REGULATING TRANSMEMBRANE ION MOVEMENT

This application is a continuation-in-part of U.S. patent application Ser. No. 923,760, filed Oct. 27, 1986, entitled "Techniques for Enhancing the Permeability of Ions Through Membranes", which is expressly incorporated herein by reference.

FIELD OF THE INVENTION

The present invention relates generally to the transmembrane movement of ions and to oscillating magnetic fields. More specifically, the present invention relates to an improved method and apparatus for regulating the transmembrane movement of ions across biochemical membranes such as cell membranes. In the inventive method and apparatus, a predetermined resonance condition for a preselected ion is maintained at a constant value, notwithstanding changes in the local magnetic field component along a predetermined axis such that transmembrane movement of the ion is regulated.

BACKGROUND OF THE INVENTION

The inventors of the present invention devised a method and apparatus for regulating the transport of a preselected ion across a cell membrane utilizing an applied, oscillating magnetic field. This remarkable achievement is disclosed in U.S. patent application Ser. No. 923,760 entitled, "Techniques for Enhancing the Permeability of Ions", which was filed on Oct. 27, 1986, and the disclosure of which is incorporated herein by reference. Therein, a method and apparatus are disclosed by which transmembrane movement of a preselected ion is magnetically regulated using a time-varying magnetic field tuned to the cyclotron resonance energy absorption frequency of the preselected ion. This important discovery brought to light the interplay of local magnetic fields and the frequency dependence of ion transport mechanisms.

Having established a method by which selective ion transport can be regulated, the present inventors discovered that certain characteristics of living tissue could be controlled by application of an oscillating magnetic field having a non-zero average value. Significantly, it was determined that selected ratios of the frequency of the applied field to the flux density of the total magnetic field passing through the tissue along a predetermined axis were capable of stimulating the growth and development of the target tissue. This was demonstrated to be effective in promoting the growth of bone tissue. As a result, U.S. patent application Ser. No. 172,268, entitled "Method and Apparatus for Controlling Tissue Growth with an Applied Fluctuating Magnetic Field" was filed on Mar. 23, 1988, the disclosure of which is incorporated herein by reference.

Therein, there is provided an apparatus for controlling the growth of living tissue. The apparatus includes magnetic field generating means such as a field coil for generating a controlled, fluctuating magnetic field which penetrates a tissue, and an associated magnetic field sensing device for measuring the intensity of the magnetic field present in the tissue. In one embodiment, the magnetic field generating means and magnetic field sensor are enclosed within a housing along with a power source.

The work with tissue growth control was extended and it was discovered that tissue development can be regulated to control the growth characteristics of non-osscous, non-cartilaginous connective tissue proper and cartilaginous tissue. These inventions are disclosed, respectively, in U.S. patent application Ser. No. 254,438, entitled "Method and Apparatus for Controlling the Growth of Non-Osseous, Non-Cartilaginous Solid Connective Tissue", which was filed Oct. 6, 1988, the disclosure of which is incorporated by reference, and in U.S. patent application Ser. No. 265,265, entitled "Method and Apparatus for Controlling the Growth of Cartilage", which was filed Oct. 31, 1988, the disclosure of which is incorporated by reference.

The inventors have now discovered that by using a feedback system to monitor the local field component of the composite magnetic field, the applied component can be automatically adjusted to maintain the proper balance to bring about transmembrane movement of ions in any application of ion transport tuning.

SUMMARY OF THE INVENTION

In one aspect, the present invention provides an apparatus for regulating the transmembrane movement of ions across a biochemical membrane such as a living cell membrane which includes magnetic field generating means, an associated magnetic field sensing means, and means for automatically adjusting the flux density of the magnetic field generating means to compensation for any deviation of the average value of the composite magnetic field intensity from a set point magnetic flux density as measured by the magnetic field density means.

In operation, the magnetic field generating means is positioned adjacent a predetermined space containing a biochemical membrane in the presence of a preselected ion to be transported. A fluctuating, directional magnetic field is then generated by the magnetic field generating means. The applied magnetic flux density is directed along a predetermined axis which passes through the membrane. In one embodiment, the applied magnetic flux density along the axis is superimposed on that component of the local or ambient magnetic field which is parallel to the predetermined axis to create a fluctuating composite field. The resultant combined magnetic flux density which is parallel to the predetermined axis and which passes through the membrane is measured by the magnetic field sensor. The magnetic field sensor determines the net average value of the magnetic flux density which passes through the membrane along the predetermined axis. In one embodiment, the frequency of the fluctuating magnetic field is set at a predetermined value and the net average value of the magnetic flux density is then regulated by adjusting the magnitude of the applied magnetic field to produce a combined magnetic field having a preselected ratio of frequency-to-field magnitude which causes transmembrane movement of the preselected ion through the membrane. In a preferred embodiment, changes in the magnitude of the local magnetic field along the predetermined axis which would otherwise alter the magnetic flux density of the combined magnetic field parallel to the predetermined axis, and which would thus produce a deviation from the desired ratio, are counterbalanced by adjustment of the magnitude of the applied, fluctuating magnetic field. This adjustment is preferably made by microprocessing means in association with both the magnetic field generating means and the magnetic field sensor. Preferred ratios of frequency-to-field magnitude are determined with reference to the equation:

$$f_c/B = q/(2\pi m)$$

where $f_c$ is the frequency of the combined magnetic field in Hertz, B is the non-zero average value of the magnetic flux density of the combined magnetic field parallel to the axis in Tesla, q/m is in Coulombs per kilogram and has a value of from about $5 \times 10^5$ to about $100 \times 10^6$. B preferably has a value not in excess of about $5 \times 10^{-4}$ Tesla. In one embodiment, the values of q and m are selected with reference to the charge and mass of a preselected ion.

In another embodiment, changes in the ambient magnetic field which would otherwise alter the ratio of frequency-to-magnetic field are counterbalanced by adjusting the frequency of the applied magnetic field to maintain the preferred ratio. The present invention also contemplates the adjustment of both frequency and field magnitude to maintain the predetermined preferred ratio. Preferably, the peak-to-peak amplitude of the AC component is in the range of about $2.0 \times 10^{-7}$ to about $2.0 \times 10^{-4}$ Tesla. The waveform is preferably substantially sinusoidal, but other waveforms are suitable.

In another aspect, the present invention provides a method of controlling the transmembrane movement of ions across a biochemical membrane including the steps of generating a fluctuating, directionally-oriented magnetic field; positioning a biochemical membrane and a preselected ion to be transported within the fluctuating, magnetic field so that the field passes through the membrane parallel to a predetermined axis that extends through the membrane; measuring the net average value of the combined magnetic flux density parallel to the predetermined axis through the membrane, where the combined magnetic field is the sum of the local magnetic field along the predetermined axis and the applied magnetic field; and automatically adjusting the frequency and/or magnitude of the applied magnetic field to produce a combined magnetic field along the axis having a predetermined ratio of frequency-to-magnitude, where the predetermined ratio causes transmembrane movement of the preselected ion.

DESCRIPTION OF THE PREFERRED EMBODIMENT

Figure 1:
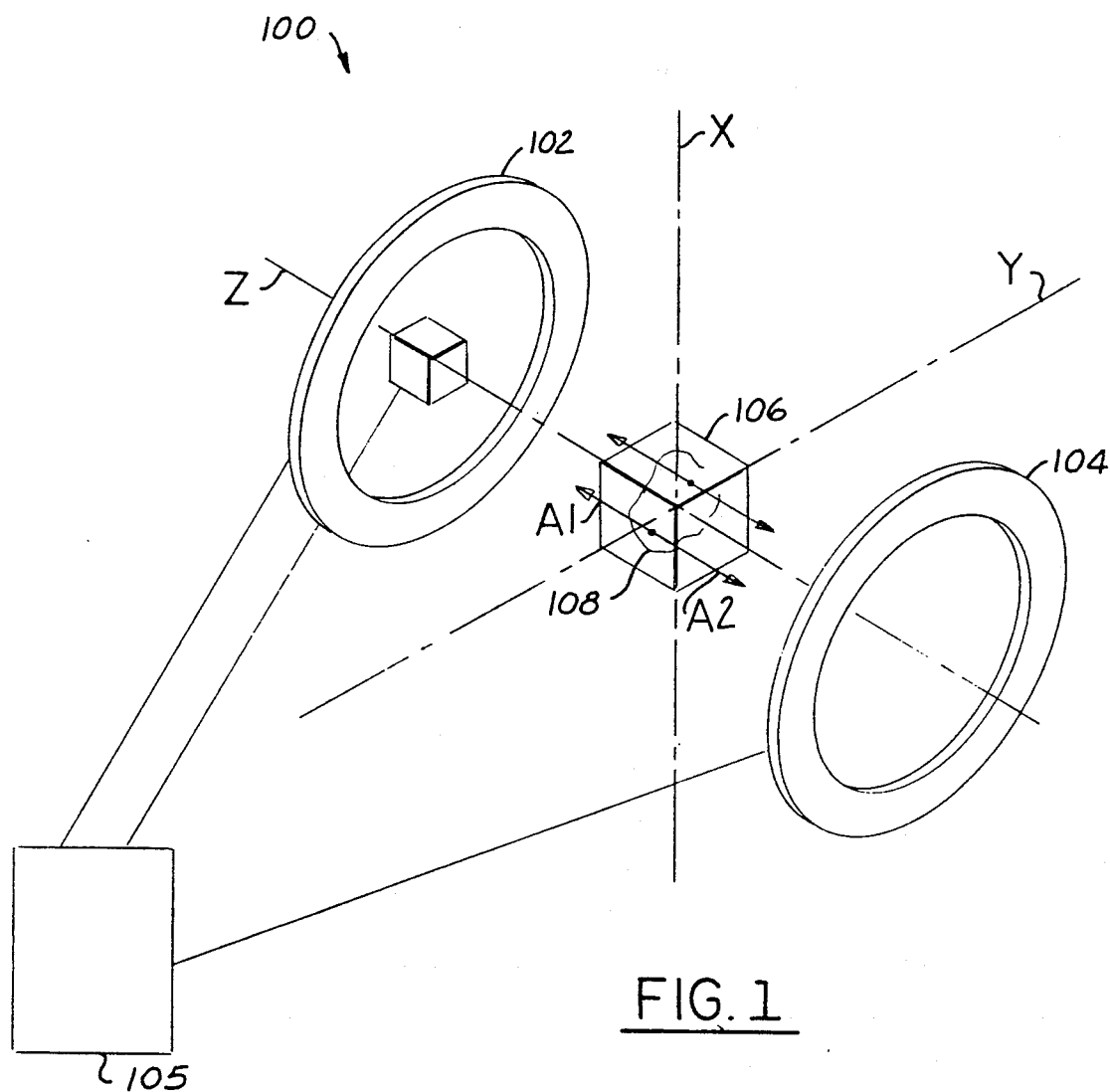
FIG. 1 is a schematic, perspective view of an exemplary living cell located in a bounded active volume in a space defining a rectangular coordinate axis system and subjected, within this active volume, to a magnetic flux density created by an electrical coil, or an equivalent permanent magnetic array or any other equivalent source of magnetic flux density.

Referring to FIG. 1 of the drawings, ion transport apparatus 100 of the present invention includes coils 102 and 104 of a Helmholtz coil pair arranged to generate an applied magnetic field directed along a longitudinal axis identified by the letter Z. The number of turns N, the diameter of the coils, the separation of the coils, and the wire gauge are only critical insofar as conventional practice requires constraints on these and other design parameters to allow optimal performance characteristics in achieving predetermined flux densities as required in the preferred practice of the present invention. These predetermined flux densities may also be achieved by conventional devices other than Helmholtz coils, such as solenoids, electromagnets, and permanent magnets.

Apparatus 100 generates a predictable, measurable and uniform magnetic flux density within active volume 106. This active volume will encompass the total volume of cells and/or tissue that are exposed to a composite flux density. A unipolar vector representing the composite magnetic flux density is illustrated by arrows A1 and A2 separated by a "." that represents the average nonzero value of the vector. The opposed arrows represent the fact that the magnitude of the composite magnetic flux changes at a predetermined rate; however, as will be explained, the direction of the flux does not change. For purposes of illustration, a single exemplary living cell 108 is shown within active volume 106.

Cell 108 contains a specific complement of intrinsic ionic species and is surrounded by a liquid or tissue medium containing ionic species required for cell and tissue function. TABLE 1 lists a typical, but incomplete, group of such ionic species suitable for use with the invention and shows the charge-to-mass ratio (q/m) of each species, in units of Coulombs per kilogram, as well as a preferred repetition rate or frequency ($f_c$), in Hz, for each species, for the specific case in which the composite magnetic flux density is $5 \times 10^{-5}$ Tesla. For any other ionic species not indicated in TABLE 1, or for any composite magnetic flux density other than $5 \times 10^{-5}$ Tesla, the preferred frequency is found using the Cyclotron Resonance Relationship.

TABLE 1

| Ionic Species | (q/m), Coulombs per Kilogram | ($f_c$), *Hz |
|---|---|---|
| Hydrogen, $H^+$ | $95.6 \times 10^6$ | 761 |
| Lithium, $Li^+$ | $13.9 \times 10^6$ | 111 |
| Magnesium, $Mg^{++}$ | $7.93 \times 10^6$ | 63.1 |
| Calcium, $Ca^{++}$ | $4.81 \times 10^6$ | 38.3 |
| Sodium, $Na^+$ | $4.19 \times 10^6$ | 33.3 |
| Chlorine, $Cl^-$ | $2.72 \times 10^6$ | 21.6 |
| Potassium, $K^+$ | $2.46 \times 10^6$ | 19.6 |
| Bicarbonate, $HCO_3^-$ | $1.57 \times 10^6$ | 12.5 |

*Resonance frequency at $5 \times 10^{-5}$ Tesla.

Figure 2:
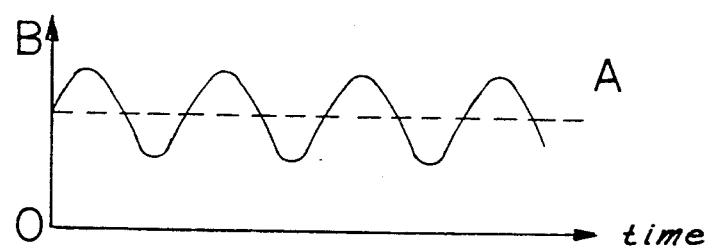
FIG. 2 illustrates the fluctuating, non-zero average value of the combined magnetic flux density.

Coils 102 and 104 are energized by controller 105 to generate a magnetic flux density within active volume 106 that varies with time as shown in FIG. 2 of the drawings. A nonzero average magnetic flux density, uniform throughout the active volume, results either from an offset sinusoidal signal or from a full-wave rectified signal applied to coils 102 and 104.

The local constant magnetic flux density will in general be superposed on the applied magnetic flux density generated by coils 102 and 104 in active volume 106. The local flux density which will generally comprise the geomagnetic field, will have one component along the direction of the Z-axis. Hence, the effect of the Z-component of the local flux density will be to change the nonzero average magnetic flux density created by coils 102 and 104 within active volume 106 to a different net average value, the value of the resultant composite magnetic field i.e. the combined local and applied field along the Z-axis.

Apparatus 100 further includes a magnetic field sensing device, shown here as magnetometer 110 which is positioned in coil 102 to measure the total or composite magnetic flux which passes through predetermined space 106 parallel to the predetermined Z-axis. It will be understood, then, that magnetometer 110 is provided to measure the composite magnetic field along the Z-axis. Magnetometer 110 then sends a signal to controller 105. As stated, the local field component either augments or decreases the applied magnetic flux unless the local field component is zero. The presence of the local field is an important consideration in the present invention. The relatively low applied flux densities and relatively precise predetermined relationships of combined flux density and frequency provided by the present invention must be maintained, notwithstanding the influence of the local magnetic field. This is achieved in essentially two preferred manners which will be explained more fully herein. Thus, magnetometer 110 is provided to determine the magnitude of the magnetic flux density of the local magnetic field.

Hence, in one embodiment of the invention, predetermined space 106 is occupied by living cell 108 and a preselected ion. Predetermined Z-axis which projects through predetermined space 106 and thus through living cell 108 is defined by the relative position of apparatus 100 with respect to cell 108. Predetermined Z-axis is the direction of the applied magnetic flux generated by field coils 102 and 104 through predetermined space 106. During this procedure, magnetometer 110 measures the total magnetic flux density parallel to the Z-axis which passes through cell 108. This total or composite magnetic flux density is the sum of the applied component and the local component. The local component may at times be in the same direction as the applied flux and at other times be in directions other than the applied flux. At times the local component may drop to zero.

Thus, changes in the local component along the Z-axis may be produced by changes in the direction of apparatus 100. Thus at $T_1$ the applied flux generated by field coils 102 and 104 may be parallel to a north-south axis and since the direction of predetermined Z-axis is defined by the direction of the applied flux, in this position, predetermined Z-axis is therefore also in the north-south direction. At $T_2$, apparatus 100 may be turned to the north causing a 90 degree rotation of field coils 102 and 104 such that the applied magnetic flux is then parallel to an east-west axis. Accordingly, predetermined Z-axis is then also in the east-west direction. In most cases, the local component of interest will have a value which is a function of directions. Therefore, the composite flux measured by magnetometer 110 along the predetermined Z-axis will change in response to changes in the position of apparatus 110 with respect to the local magnetic field. The net average value of magnetic flux density is accordingly regulated to compensate for the change in composite flux.

Transmembrane ion transport is achieved by creating a fluctuating combined or composite magnetic field having a magnetic flux density parallel to predetermined Z-axis, where the combined magnetic flux density along the Z-axis is maintained at a predetermined relationship to the frequency of the fluctuations. The combined magnetic flux density parallel to the Z-axis has a non-zero net average value. As illustrated in FIG. 2 of the drawings, the composite magnetic field of the present invention can be thought of as a static field having reference level "A" on which a fluctuating magnetic field is superimposed. It comprises an ac component which varies in amplitude but not direction and a dc reference around which the ac component varies. Reference level A is the non-zero average value of the flux density. Therefore, it will be understood that the non-zero average or net average value of the composite magnetic flux density along the Z-axis is utilized since the magnitude of the composite flux density changes at a predetermined rate due to oscillation or fluctuation of the applied magnetic flux. This reflects the fact that although the composite magnetic flux density along the axis is oscillating at a controlled rate, the composite field is regulated by the intensity of the applied field to ensure that the composite field is always unipolar; that is, the composite field is always in the same direction along the Z-axis.

As stated, it has been found that rather precise relationships of the flux density of the combined magnetic field to the frequency of the fluctuations are used in the present invention to regulate transmembrane ion transport. These ratios of frequency to composite flux density are found in accordance with the following equation:

$$f_c/B = q/(2\pi m)$$

where $f_c$ is the frequency of the combined magnetic field in Hertz, B is the net average value of the magnetic flux density of the combined magnetic field parallel to the Z-axis in Tesla, and q/m has a value of from about $5 \times 10^5$ to about $100 \times 10^6$ Coulombs per kilogram. B preferably has a value not in excess of about $5 \times 10^{-4}$ Tesla. By exposing cell 108 to a regulated magnetic flux density having these characteristics, the predetermined ion is transported through cell membrane.

It will be appreciated by the prior explanation of preferred embodiments of the present invention and from the equation for establishing a cyclotron resonance relationship, that either the frequency of the fluctuating magnetic field or the magnitude or intensity of the magnetic flux density along the predetermined axis, or both the frequency and the intensity of the flux density, can be adjusted to provide a magnetic field within volume 106 which has the desired characteristics. However, as stated, it is preferred to maintain a constant frequency which thus requires that the intensity of the applied magnetic flux density be adjusted to compensate for changes in the local magnetic field in order to maintain a constant ratio of frequency to magnetic flux density. For example, if it necessary to maintain a frequency of 15 Hz and an average flux density of $1.95 \times 10^{-5}$ Tesla to affect ion transport, changes in the local field which would otherwise cause unwanted deviations in the combined magnetic flux density must be corrected by increasing or decreasing the applied magnetic flux density accordingly. This is performed by a microcontroller in controller 105 in connection with both the field generating means and the field-sensing device. Alternatively, as stated, if changes in the combined magnetic flux density along the axis will occur due to changes in the orientation of apparatus 110 with respect to the preexisting local magnetic field, the frequency of the oscillations can then be changed so that the preferred ratio is maintained. It will be understood that detection of changes in the magnetic field due to changes in the ambient component should be at intervals frequent enough to provide a frequency-to-magnetic field ratio which is substantially constant, notwithstanding the changes in the local field component.

It may also be appropriate in some instances to reduce components of the local magnetic field which are not parallel to the axis to zero through the use of additional coils positioned at right angles to coils 102 and 104 to create an opposite but equal field and that one coil of each additional coil pair may be equipped with a magnetometer, although this is not deemed necessary. It may also be suitable to reduce the local magnetic field component to zero along the Z-axis using additional coils or the like.

Figure 3:
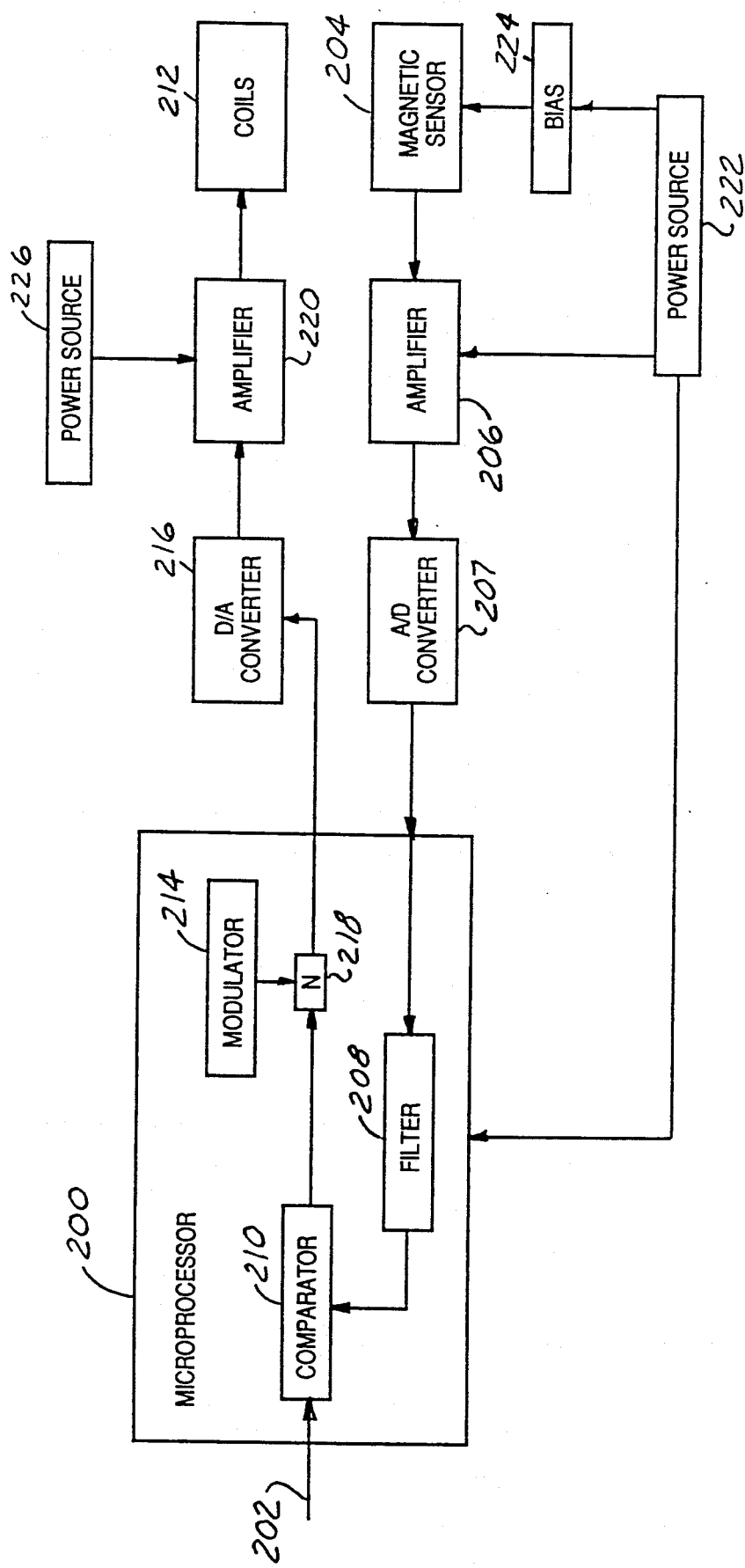
FIG. 3 is a block diagram of an embodiment of the present invention in which the circuit of the inventive apparatus is arbitrarily divided into convenient functional sections.

Referring now to FIG. 3 of the drawings, a block diagram is shown which depicts one preferred arrangement of the circuits of apparatus 100 in functional segments. Numerous other circuit arrangements may be possible if the principles of the present invention are faithfully observed. Microcontroller or microprocessor 200 is seen by which the composite magnetic field is maintained at a constant predetermined level despite changes in the ambient component as previously described. In this respect, input 202 is provided by which a set point value of the predetermined composite magnetic flux density along a predetermined axis through the membrane is input into microprocessor 200. As will be shown, the composite field strength is compared to this set point value to generate an error equal to the difference in the set point value and the measured value of the composite magnetic flux density along the axis.

As stated, a magnetic field sensor, shown here as block 204, is provided by which the magnitude of the composite field which passes through cell 108 along the Z-axis is measured. It is preferred that magnetic field sensor 204 comprise a Hall-effect device which, as will be known by those skilled in the art, produces an analog signal. The magnetic field sensor 204 constantly monitors the composite magnetic field, sending a signal to microprocessor 200. It will be understood that the output of a Hall-effect magnetic sensor is relatively small; thus, magnetic field sensor amplifier 206 is provided by which the signal from magnetic field sensor 204 is amplified, for example, up to three thousand times its original value. Since a Hall-effect device produces an analog signal, analog-to-digital converter 207 is provided by which the amplified signal from magnetic field sensor 204 is converted to a digital signal which can be used by microprocessor 200. It is preferred that the analog-to-digital converter be provided onboard the microprocessor chip.

As will be appreciated, the amplification of the magnetic field sensor signal may produce an unwanted noise level. Also, sudden changes in the magnetic field intensity may occur which make it difficult to determine the true average value of the composite magnetic flux density. Hence, the signal from analog-to-digital convertor 206 which is input into microprocessor 200 is filtered by software filter 208 to remove shot noise and sudden fluctuations in the composite field detected by magnetic field sensor 204. Although it is preferred that filter 208 comprise software in microprocessor 200, a discrete filter could be used. In this embodiment, software filter 208 is a digital filter, preferably an integrator with a time constant of approximately 0.5 seconds. In other words, the changes in the magnitude of the composite magnetic field which are compensated for by increasing or decreasing the applied field are long-term changes of 0.5 seconds or more which result primarily from changes in the orientation of apparatus 100 with respect to the ambient field component. Hence, the time constant of filter 208 should be such that momentary fluctuations are filtered out.

Microprocessor 200 includes logic which calculates the non-zero net average value of the composite magnetic flux density. This non-zero average value is then compared at comparator 210 in microprocessor 200 to the predetermined dc reference or offset value which is input into microprocessor 200 via input 202. It should be noted that this reference value is preferably established by dedicated circuitry in microprocessor 200, although variable input means could be included by which the set point value could be changed. An error statement is then generated defining the difference in the measured value of the composite magnetic flux density and the set point or reference value. Microprocessor 200 then determines the magnitude of the output necessary to drive magnetic field generating coils, shown here as block 212, to bring the composite magnetic flux density back to the set point W and produces a signal to increase or decrease the magnetic flux density.

Software field modulator or oscillator 214 is provided by which an ac or fluctuating component is superimposed on the digital output signal which is input into digital-to-analog converter 216. From the previous discussion of the present invention, it will be understood that software field modulator 214 of microprocessor 200 in the preferred embodiment of the present invention is preset to a fixed, predetermined frequency to produce the desired predetermined, ion transport ratio of frequency-to-magnetic flux density value. In another embodiment, the feedback system of the present invention is such that changes in the composite magnetic flux density are measured, whereupon microprocessor 200 determines the necessary change in frequency to maintain the predetermined relationship. In that embodiment, software field modulator 214 produces the requisite ac frequency. It is again preferred that digital-to-analog converter 216 be provided on-board the microprocessor chip. Hence, software field modulator 214 provides the ac component at node 218.

The signal from digital-to-analog converter 216 is fed to voltage-to-current amplifier 220, the output of which drives magnetic field generating coils 212 in the desired manner. Hence, the composite field is held substantially constant despite changes in the ambient component.

While several arrangements of power sources are suitable, it is preferred that power supply 222 be provided to power magnetic field sensor amplifier 206, microprocessor 200 and magnetic field sensor 204, the latter via bias circuitry 224. A separate power source 226 is preferred for voltage to current amplifier 220.

Having fully described the apparatus of the present invention, including its manner of construction, operation and use, the method of the present invention will now be described. It is to be understood that this description of the method incorporates the foregoing discussion of the novel apparatus. In this aspect, the present invention provides a method of regulating the transmembrane movement of a preselected ion across a biochemical membrane such as the cell membrane of a living cell. This is achieved in one embodiment by generating a fluctuating, directionally-oriented magnetic field which projects through the target biochemical membrane. A number of magnetic field generating means are suitable for this purpose. The magnetic field so generated has a magnetic flux density of precisely controlled parameters which passes through the target membrane parallel to a predetermined axis projecting through the tissue. As will be known by those skilled in art and as has been clearly explained, the local magnetic field to which the membrane is subjected will have a component which is parallel to the predetermined axis and which thus aids or opposes the applied or generated magnetic field along the axis. At times, the local component may be zero. In the method of the present invention, the density of this combined magnetic flux, and more specifically the average non-zero value of the combined magnetic flux density, is controlled to provide a precise relationship between the flux density along the axis and the frequency of the applied magnetic field which is oscillating at a predetermined value. Most preferably this is accomplished by automatically adjusting the intensity of the applied field to compensate for changes in the local field. Thus, in one embodiment, the present invention provides a method of regulating transmembrane movement of a preselected ion by creating a magnetic field which penetrates the target membrane and which has a predetermined relationship between frequency of oscillation and average flux density. The predetermined relationship or ratio of frequency-to-field magnitude is determined with reference to the equation:

$$f_c/B = q/(2\pi m)$$

where $f_c$ is the frequency of the combined magnetic field along the predetermined axis in Hertz, B is non-zero net average value of the magnetic flux density of the combined magnetic field parallel to the axis in Tesla, q/m is in Coulombs per kilogram and has a value of from about $5 \times 10^5$ to about $100 \times 10^6$. B preferably has a value not in excess of about $5 \times 10^{-4}$ Tesla.

In order to create a fluctuating magnetic field having the desired parameters, the composite magnetic field parallel to the predetermined axis is constantly monitored. As stated, this is preferably carried out with a Hall effect device or the like which produces an analog signal. This analog signal is periodically sampled by microprocessing means which then calculates the necessary frequency and/or magnitude of the applied magnetic field to maintain the preprogrammed, predetermined ratio previously described. Of course, it will now be understood that it is the combined magnetic flux which is sensed by the magnetic field sensor. The magnetic field generating means is used to adjust the magnitude of this composite field where appropriate.

In one embodiment, the method includes controlling the average value of the applied magnetic flux density along a predetermined axis to maintain a predetermined ratio of frequency-to-composite magnetic flux density. In another embodiment, the frequency of the fluctuations is adjusted to maintain this relationship in which changes in the combined magnetic flux density due to changes in the local magnetic field are detected. Moreover, a combination of these two methods may be used wherein both the frequency and the magnitude of the magnetic field flux density are adjusted to maintain the predetermined relationship of the present invention.

Hence, in addition to the apparatus of the present invention, the present invention provides a method for controlling transmembrane movement of a preselected ion across a biochemical membrane which includes the steps of creating a fluctuating magnetic field of predetermined frequency and flux density along an axis projecting through a predetermined volume and positioning a target biochemical membrane such as a living cell within this predetermined space such that it is exposed to the fluctuating magnetic field. The predetermined parameters of the fluctuating magnetic field are determined by measuring the net average value of the combined magnetic flux density parallel to the predetermined axis through the tissue, where the combined magnetic field is the sum of the local magnetic field along the predetermined axis and the applied magnetic field with a magnetic sensing means. The frequency and/or magnitude of the applied magnetic flux density is then automatically controlled by a microprocessor to produce a combined magnetic field along the axis having a predetermined ratio of frequency-to-flux density. This predetermined ratio causes transmembrane movement of the preselected ions.

While particular embodiments of this invention are shown and described herein, it will be understood, of course, that the invention is not to be limited thereto, since many modifications may be made, particularly by those skilled in the art, in light of this disclosure. It is contemplated, therefore, by the appended claims, to cover any such modifications as fall within the true spirit and scope of this invention.

What is claimed is:

1. An apparatus for enhancing the transfer of a predetermined ion having a predetermined charge-to-mass ratio through a membrane located in a space subjected to a local magnetic field, the space defining at least one reference path passing through the membrane, the reference path extending in a first direction and also extending in a second direction opposite the first direction, said apparatus comprising:

field creating means responsive to signals for creating a magnetic field which, when combined with the local magnetic filed, results in a resultant magnetic field having a flux density with at least one component representable by a component vector having a direction extending in the first direction along the path and having a magnitude that fluctuates at a predetermined rate to create a nonzero average value, the ratio of the predetermined rate to the nonzero average value having a predetermined relationship which is a function of the charge-to-mass ratio of the predetermined ion;

signal generating means for generating said signals, at least some of said signals being generated at the predetermined rate;

magnetic sensing means adapted to measure a magnetic flux density having a nonzero average value for measuring the magnitude of said one component of said resultant magnetic field; and means in association with said field creating means for automatically adjusting the magnitude of said one component of said resultant magnetic field to maintain said predetermined relationship.

2. The apparatus recited in claim 1, wherein said magnetic sensing means includes a Hall-effect device.

3. The apparatus recited in claim 2, wherein said automatically adjusting means includes a microcontroller.

4. An apparatus for the transmembrane movement of a preselected ion, comprising:

a pair of field coils for generating an applied magnetic flux in a predetermined space and parallel to a predetermined axis which projects through said predetermined space, said predetermined space being occupied by a biochemical membrane and a preselected ion;

a magnetic field-sensing device adapted to measure a magnetic flux density having a nonzero average value for measuring magnetic flux density parallel to said predetermined axis in said predetermined space; and microprocessing means, including means for oscillating said applied magnetic flux, in communication with said field coils and said field-sensing device for creating and automatically maintaining a predetermined relationship which is a function of the frequency of said magnetic field and the intensity of said magnetic flux density to provide a fluctuating magnetic field which causes transmembrane movement of said preselected ion through said biochemical membrane.

5. An apparatus for enhancing the transfer of a predetermined ion having a predetermined charge-to-mass ratio through a membrane located in a space subjected to a local magnetic field, the space defining at least one reference path passing through the membrane, the reference path extending in a first direction and also extending in a second direction opposite the first direction, said apparatus comprising:

field creating means responsive to signals for creating a magnetic field which, when combined with the local magnetic field, results in a resultant magnetic field having a flux density with at least one component representable by a component vector having a direction extending in the first direction along the path and having a magnitude that fluctuates at a predetermined rate to create a nonzero average value, the ratio of the predetermined rate to the nonzero average value having a predetermined relationship which is a function of the charge-to-mass ratio of the predetermined ion;

signal generating means for generating said signals, at least some of said signals being generated at the predetermined rate;

magnetic sensing means adapted to measure to flux density having a nonzero average value for measuring the magnitude of said one component of said resultant magnetic field; and means in association with said field creating means for automatically adjusting the frequency of said fluctuation to maintain said predetermined relationship.

6. The apparatus recited in claim 5, wherein said magnetic sensing means includes a Hall-effect device.

* * * * *